United States Patent
Sinha

[19]

[11] Patent Number: 6,117,089
[45] Date of Patent: Sep. 12, 2000

[54] METHOD FOR NONINVASIVE INTRACRANIAL PRESSURE MEASUREMENT

[75] Inventor: Dipen N. Sinha, Los Alamos, N. Mex.

[73] Assignee: The Regents of the University of California, Los Alamos, N. Mex.

[21] Appl. No.: 08/428,940

[22] Filed: Apr. 25, 1995

[51] Int. Cl.[7] .................................................... A61B 5/00
[52] U.S. Cl. .......................... 600/561; 600/587; 600/595
[58] Field of Search ..................... 128/660.02, 660.03, 128/748, 774; 73/772, 716

[56] References Cited

U.S. PATENT DOCUMENTS

| | | | |
|---|---|---|---|
| 4,971,061 | 11/1990 | Kageyama et al. | 128/660.02 |
| 5,074,310 | 12/1991 | Mick | 128/748 |
| 5,309,898 | 5/1994 | Kaufman et al. | 601/2 |
| 5,388,583 | 2/1995 | Ragauskas et al. | 128/661.05 |

OTHER PUBLICATIONS

"Noninvasive Pressure Measurement", Devine et al, IBM Technical Disclosure Publication, Jan. 1978 vol. 20, No. 8.

*Primary Examiner*—Cary O'Connor
*Assistant Examiner*—Pamela L. Wingood
*Attorney, Agent, or Firm*—Samuel M. Freund

[57] ABSTRACT

An ultrasonic-based method for continuous, noninvasive intracranial pressure (ICP) measurement and monitoring is described. The stress level in the skull bone is affected by pressure. This also changes the interfacial conditions between the dura matter and the skull bone. Standing waves may be set up in the skull bone and the layers in contact with the bone. At specific frequencies, there are resonance peaks in the response of the skull which can be readily detected by sweeping the excitation frequency on an excitation transducer in contact with a subject's head, while monitoring the standing wave characteristics from the signal received on a second, receiving transducer similarly in contact with the subject's head. At a chosen frequency, the phase difference between the excitation signal and the received signal can be determined. This difference can be related to the intracranial pressure and changes therein.

4 Claims, 4 Drawing Sheets

METHOD FOR NONINVASIVE INTRACRANIAL PRESSURE MEASUREMENT

FIELD OF THE INVENTION

The present invention relates generally to the measurement of intracranial pressure (ICP) and, more particularly, to a method using ultrasonics for continuous, noninvasive intracranial pressure measurement and monitoring. This invention was made with government support under Contract No. W-7405-ENG-36 awarded by the U.S. Department of Energy to The Regents of The University of California. The government has certain rights in the invention.

BACKGROUND OF THE INVENTION

Elevated intracranial pressure (ICP) is a leading cause of irreversible brain damage after trauma, brain disorder, or disease. In severe cases, disability and death may occur. ICP monitoring provides early warning of the onset of deteriorating conditions which, once recognized and diagnosed, can often be effectively treated to prevent neurological impairment. Certain medical conditions, such as meningitis, encephalitis, Reye's syndrome, diabetic encephalopathy, hepatic encephalopathy, near drowning, hydrocephalus, cerebral infarction, subarachnoid hemorrhage, among others, also require ICP to be monitored. Additionally, the time development of a patient's ICP is often of significance to emergency room physicians.

Currently, ICP monitoring is achieved using either sensors implanted within the cranium or external sensors connected to the measurement site in the cranium with a fluid-filled catheter. Both approaches are invasive, generating risk of intracranial infection and pain for the patient, and require neurosurgical expertise for their implantation. Moreover, long periods of patient movement restriction are often required. Most typical among the invasive procedures is the lumbar puncture where a catheter having a pressure-sensing device is placed in the lumbar subarachnoid space. Variations of this technique include drilling a hole in the skull and inserting the catheter.

Existing techniques for noninvasive estimation of ICP include the assessment of level of consciousness on neurologic examination, opthalmoscopic examination of the optical fundi for evidence of papilledema in adults, and the palpation of the fontanelles and skull sutures in infants. Unfortunately, these clinical methods are highly qualitative, do not necessarily correlate directly with more sophisticated analytic ICP measurements, and cannot be performed on a continuous basis.

Several researchers have investigated the use of ultrasound for noninvasively monitoring ICP with varying success. For example, H. Kuchiwaki et al., in "Continuous Recording of Changes in Intracranial Pressure Using Interference Echoes of Ultrasonic Wave: A Preliminary Report of Practicality and Clinical Evaluation," J. Clin. Ultrasound 20, 447 (1992), have demonstrated that a correlation exists between the amplitude of ultrasound interference echoes and the level of ICP using a combination of pulse-echo, high-speed digitizer and time-windowing techniques. The authors attach the transducers to the surface of the skull bone using cyanoacrylate. No direct means for calibration are provided.

Another ultrasonic technique has been described by John H. Cantrell et al., in "Measuring Intracranial Pressure and Volume Noninvasively," NASA Tech Briefs, p. 78 (June 1994) at the NASA Langley Research Center. An ultrasonic tone-burst is directed through the cranium and the phase of the ultrasound signal is monitored subsequent to its traversal. This phase relates to the time required for the tone burst to be reflected from the inside surface of the cranium. Variation in ICP alters the stress level experienced by the skull bone and affects its characteristic sound propagation. Feed-back loop electronics are employed for determining the phase of the received echo using the same transducer that is used for generating the initial signal from outside the skull. A calibration may be achieved by applying a known amount of external mechanical pressure to the skull. No quantitative data are reported, however. Since only a small area of the skull bone (the area of transducer contact) is probed by the ultrasound, the sensitivity is poor, and sophisticated electronics are required for monitoring small changes in sound velocity in the body of the skull due to changes in pressure. Pulsed or tone-burst techniques also require high voltages (–100 V or higher) for proper excitation.

Accordingly, it is an object of the present invention to provide a noninvasive method for measuring changes in intracranial pressure.

Another object of the invention is to provide a noninvasive method for monitoring intracranial pressure in real time.

Additional objects, advantages and novel features of the invention will be set forth in part in the description which follows, and in part will become apparent to those skilled in the art upon examination of the following or may be learned by practice of the invention. The objects and advantages of the invention may be realized and attained by means of the instrumentalities and combinations particularly pointed out in the appended claims.

SUMMARY OF THE INVENTION

To achieve the foregoing and other objects, and in accordance with the purposes of the present invention, as embodied and broadly described herein, the method for measuring changes in intracranial pressure of a subject hereof may include the steps of: applying an ultrasonic, oscillatory excitation to the head of the subject, thereby generating a standing-wave pattern in the skull bone of the subject, detecting the resulting vibrations in the skull bone at a chosen distance from the region of generating the standing-wave pattern, choosing an ultrasonic frequency such that the detected vibrations have a chosen amplitude, and measuring the phase difference between the detected vibrations and the applied ultrasonic excitation, whereby changes in the intracranial pressure may be related to changes in the measured phase difference.

Benefits and advantages of the present invention include low-cost implementation of ICP measurements in hospital operating rooms, patient bed-side, emergency rooms, and pre-hospital settings, thereby reducing the burden of rehabilitation and lost productivity associated with undiagnosed, untreated elevated ICP leading to brain damage.

BRIEF DESCRIPTION OF THE DRAWINGS

The accompanying drawings, which are incorporated in and form a part of the specification, illustrate the embodiments of the present invention and, together with the description, serve to explain the principles of the invention. In the drawings.

DETAILED DESCRIPTION

Briefly, the present invention includes an ultrasonic method for monitoring ICP. Pressure affects the stress level in the skull bone and also changes the interfacial conditions between the dura matter and the skull bone. Over a small area of the skull, the thickness of the bone is relatively uniform and can be considered almost parallel. This allows for standing waves to be set up in the skull bone and the tissue layers in contact with the bone. At specific frequencies, there are resonance peaks in the response of the skull which can be detected by sweeping the excitation frequency on an excitation transducer in contact with the subject's head, while monitoring the standing wave characteristics of the signal received on the second, receiving transducer, likewise in contact with the subject's head (both, typically on the forehead). One such characteristic is the phase difference between these two signals at a chosen frequency which has been found to be related to the intracranial pressure and changes therein. If sufficient skull bone area is sampled, the effect is magnified and measurements can be made using low-level (~1 V), continuous-wave excitation.

Figure 1:
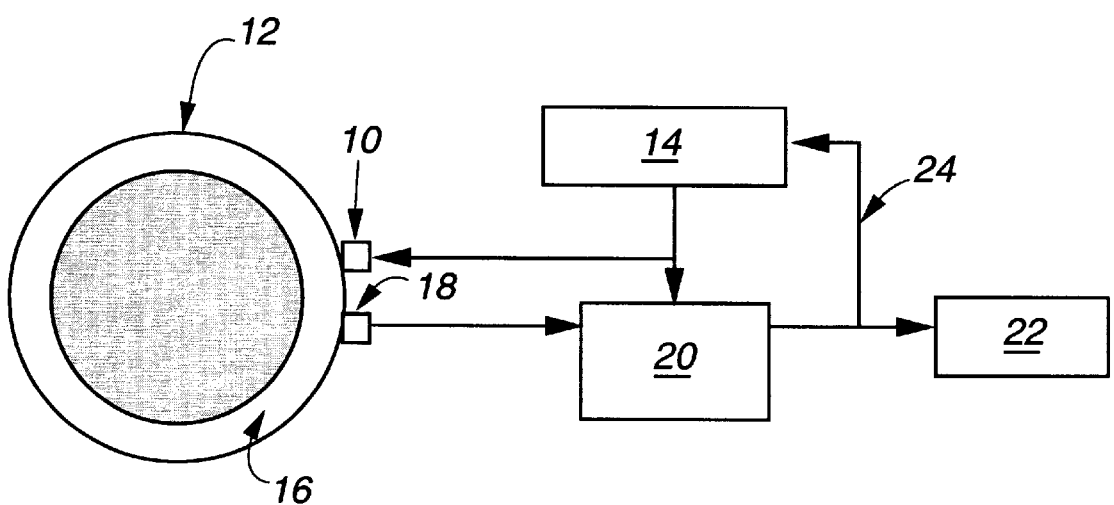
FIG. 1 is a schematic representation of an apparatus suitable for practicing the method of the present invention.

Reference will now be made in detail to the present preferred embodiments of the present invention, examples of which are illustrated in the accompanying drawings. Turning now to FIG. 1, a schematic representation of the apparatus of the present invention is illustrated. Transmitting transducer, 10, is placed against a bony portion of the head, such as the forehead, of a subject whose ICP is to be measured, and a continuous ultrasonic sine-wave is impressed in the transducer by oscillator, 14. Receiving transducer, 18, is placed anywhere on the bony portion of the head, although a position 1–3 cm from transducer, 10, is convenient since the transducers can then be applied using a simple holder therefor (not shown). Videoscan, V-103 transducers from Panametrics, Inc. were employed for the described measurements, although many commercial transducers are adequate. Transducers are attached to the forehead with a very thin layer of coupling gel or any type of grease. Perspiration has been found to provide good coupling between the transducers and the skin on the forehead. Coupling is not a critical issue.

Standing waves generated in the skull bone are detected by transducer, 18, and the phase difference between the transmitted oscillatory signal and the received signal is determined by phase detector, 20. Computer, 22, controls the data-taking process (applied frequency, scan rate, etc.) and analyzes the output from phase detector, 20.

Figure 2:
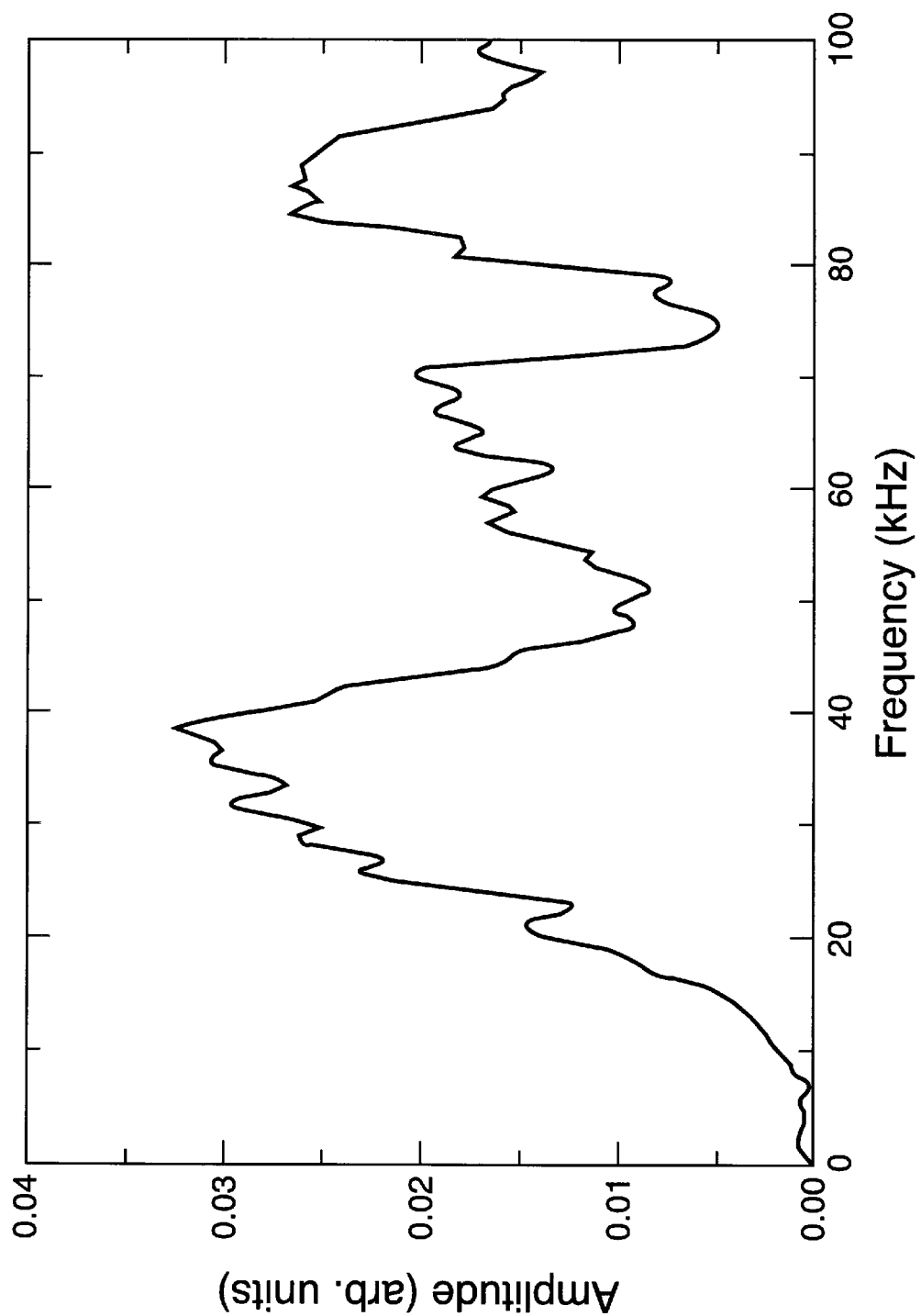
FIG. 2 shows the resonant response of the skull of a living subject as a function of excitation frequency utilizing the apparatus shown in FIG. 1 hereof.

FIG. 2 shows the detected vibration amplitude appearing on the receiving transducer from the head of a human subject as a function of the applied frequency to the transmitting transducer. The large, broad peaks are due to standing waves set up within the skull bone and the scalp. The smaller peaks are due to standing waves set up along the circumference of the cranium. The resonance peaks are typically broad since the skull thickness is not entirely uniform, and as a result of the fact that the scalp on the outside and the dura matter within the skull contribute to signal damping. If a frequency corresponding to a skull bone resonance is selected, effects of stress due to change in ICP are substantially magnified. This effect is analogous to the amplification of in a resonating system and is directly proportional to the Q (quality factor) of the system.

Resonance (standing wave) frequencies can be determined automatically using the apparatus described in FIG. 1, hereinabove, where the phase difference between the excitation signal and the received signal from phase detector, 20, is directed into oscillator, 14, by means of feedback loop, 24. Once any one of the several resonance frequencies is found, that particular frequency is kept fixed and only the phase output is monitored. This frequency can also be determined manually without using any feedback mechanism by monitoring the amplitude of the receiver transducer output using an ac voltmeter. Typical transducer separations are approximately 2 cm. If there is a change in the ICP, the resultant effect on the skull bone is observed through the phase difference between the two transducers. Because of the resonances, the effect of internal pressure changes on the entire cranium can easily be observed with low applied energy. Typical excitation signals are approximately 1 V rms, which are not detectable by a patient. The ICP acts radially on the skull bone, stressing it a small amount. The consequent effect on the skull's elastic properties shifts the resonant frequencies, which shift is readily detected by phase measurements. Phase measurements can also be accomplished utilizing a tone burst consisting of several cycles of a sine-wave frequency for the excitation process. This further reduces the applied power level requirements which can then be as low as 1/100th of the continuous-wave excitation, thereby improving safety for long-term monitoring requirements. Overall, the method of the present invention requires very low-level excitation and thus is inherently safe for the subject.

Figure 3:
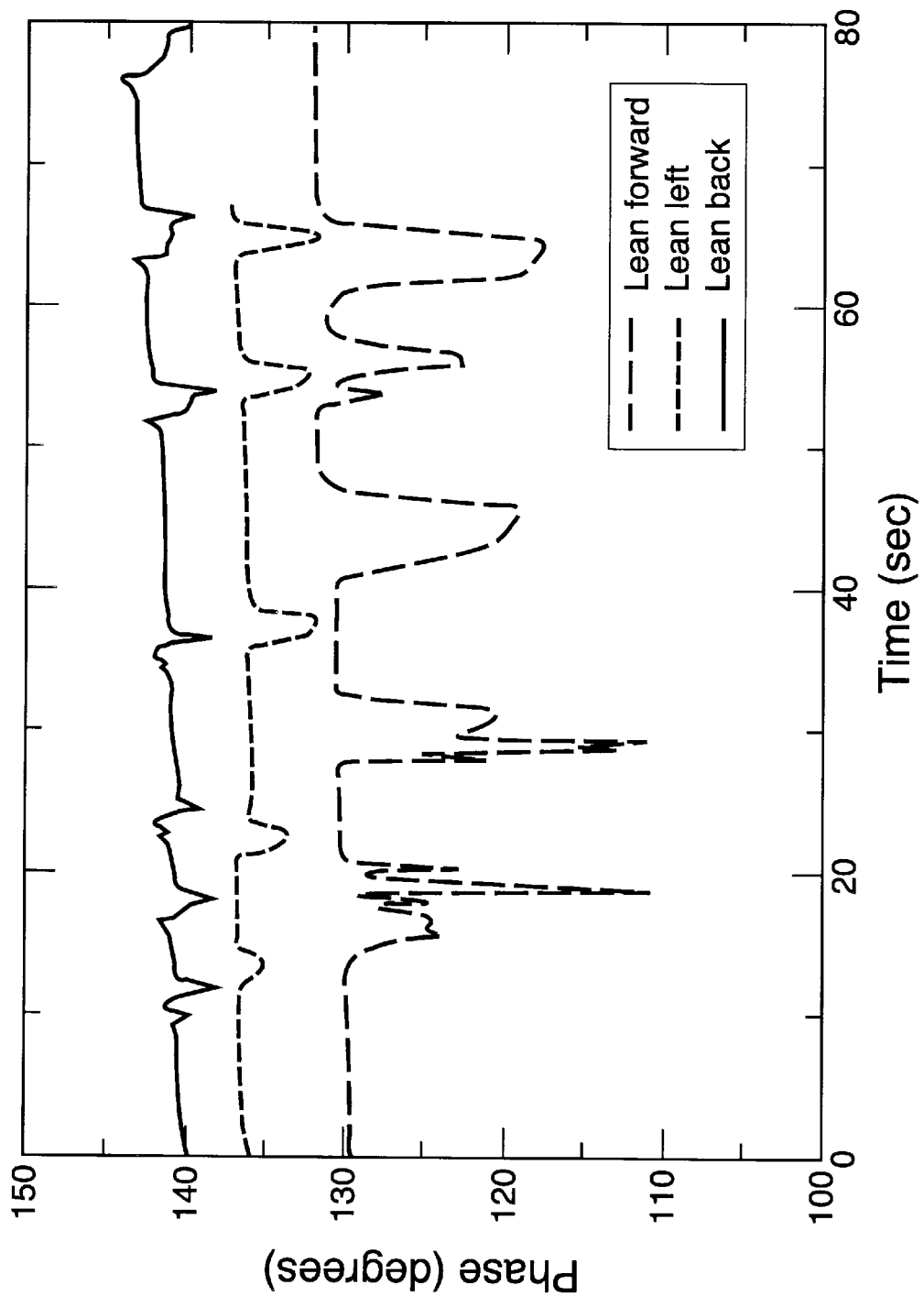
FIG. 3 shows measurement of the phase relationship between the applied ultrasonic signal and the signal appearing on the receiving transducer as a function of head position.

FIG. 3 presents phase difference measurements as a function of head position; the solid line corresponds to the head in a leaning back position, whereas the dotted line corresponds to the head being leaned to one side, and the dashed line corresponds to the head being leaned in the forward direction. Changes in the ICP are induced by changing the orientation of the head. Normally, a person undergoes a change of 15 mm in ICP by moving from a lying position to a sitting position. In the situation used to generate the data illustrated in FIG. 3, the subject was seated. In each case, the subject returned to the normal upright sitting position after a brief change in orientation. The various dips and spikes correspond to the change in ICP when there is a change in orientation. As might be expected, leaning all the way forward (where the subject's head was pointing downward) produced the largest change. As may be observed from the figure, the phase value returned to its base level when the head was returned to the upright position. This feature is important for long-term ICP monitoring. The measurements were taken at an excitation frequency of 64.25 kHz with an excitation signal amplitude of 2 V peak-to-peak.

Figure 4:
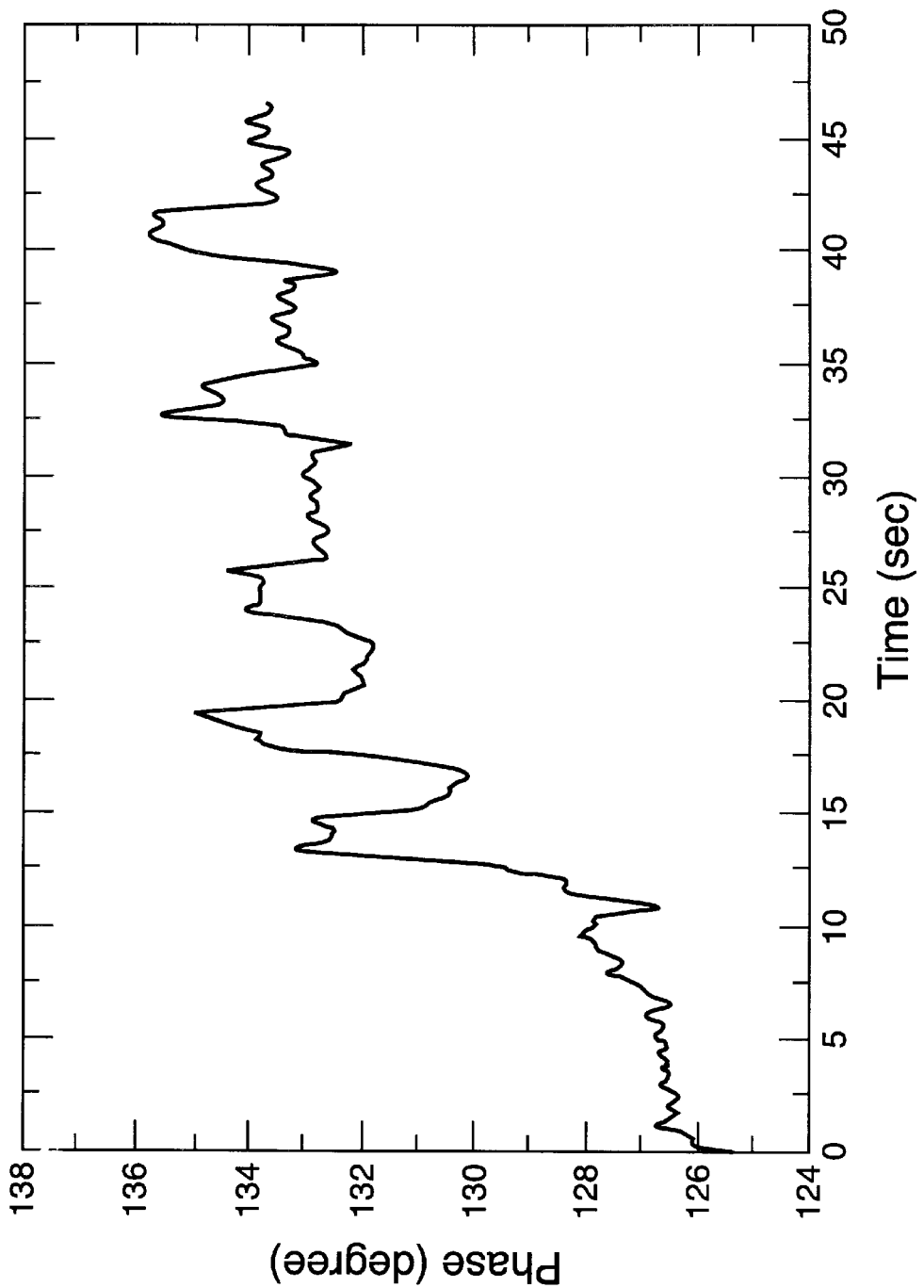
FIG. 4 shows measurement of the phase relationship between the applied ultrasonic signal and the signal appearing on the receiving transducer for an upright head to which pressure is applied using a finger.

FIG. 4 shows the effect on the ICP of external pressure being applied to the head more than 5 cm away from the transducers. The pressure was produced by pressing fingers against an upright head. Again, the excitation frequency was 64.25 kHz, and the detected signal was 2 V peak-to-peak. The peaks in the curve correspond to applications of finger pressure. Since the subject's head was not fixed in space, there were head movements during the procedure which resulted in the observed upward slow rise of the baseline.

The finger pressure was gentle. The small oscillatory peaks correspond to the pulse rate of the subject.

It should be mentioned that FIG. 4 presents peaks, whereas FIG. 3 shows dips. This is a result of the direction of the force applied to the skull bone. The internal pressure change due to a change in ICP presses outward from inside the skull and expands the skull. By contrast, an external force pressing inwardly produces a contraction of the skull bone. Therefore, a calibration measurement can be obtained quite easily. Instead of finger pressure, a calibrated weight may be utilized. It is also possible to use a head band from which a known tension is applied to the skull. The resolving power of the present method is estimated to be approximately 0.1 mm ICP which is comparable to most invasive methods of ICP monitoring.

The foregoing description of the invention has been presented for purposes of illustration and description and is not intended to be exhaustive or to limit the invention to the precise form disclosed, and obviously many modifications and variations are possible in light of the above teaching. For example, after studying the present disclosure, it would be apparent to one having skill in the art that the transducers could be modified in such a way that they could be worn by pilots and drivers of public transportation vehicles such as buses and trains, thereby providing indication of when a person is failing asleep (e.g., nodding) and thus avoid accidents.

The embodiment was chosen and described in order to best explain the principles of the invention and its practical application to thereby enable others skilled in the art to best utilize the invention in various embodiments and with various modifications as are suited to the particular use contemplated. It is intended that the scope of the invention be defined by the claims appended hereto.

What is claimed is:

1. A method for measuring changes in intracranial pressure of a subject, which comprises the steps of:
   a. applying an ultrasonic, oscillatory excitation to the head of the subject, thereby generating a standing-wave in the skull bone of the subject;
   b. detecting the resulting vibration in the skull bone at a chosen distance from the region of generating the standing-wave pattern;
   c. choosing a frequency for said step of ultrasonic, oscillatory excitation such that the detected vibration corresponds to a resonance in the skull bone; and
   d. measuring the phase difference between the detected resonant vibration and the applied ultrasonic excitation, whereby changes in the intracranial pressure may be related to changes in the measured phase difference.

2. The method for measuring changes in intracranial pressure of a subject as described in claim 1, wherein said steps of applying ultrasonic, oscillatory excitation to the head of the subject, and detecting the resulting vibrations in the skull bone of the subject are performed using piezoelectric transducers.

3. The method for measuring changes in intracranial pressure of a subject as described in claim 2, wherein the transducers are contacted to the subject's head using a coupling gel.

4. The method for measuring changes in intracranial pressure of a subject as described in claim 1, wherein said step of choosing an ultrasonic frequency such that the detected vibrations have a chosen amplitude is accomplished by choosing the region of maximum amplitude of a resonance in the skull bone.

\* \* \* \* \*